United States Patent
Werle et al.

[11] Patent Number: 4,492,643
[45] Date of Patent: Jan. 8, 1985

[54] BISMELAMINE STABILIZERS

[75] Inventors: Peter Werle, Getnhausen; Holger Focke, Bruchköbel; Klaus Popp, Rodenbach; Wolfgang Merk, Hanau, all of Fed. Rep. of Germany

[73] Assignee: Degussa Aktiengesellschaft, Frankfurt, Fed. Rep. of Germany

[21] Appl. No.: 438,349

[22] Filed: Nov. 1, 1982

[30] Foreign Application Priority Data

Nov. 5, 1981 [DE] Fed. Rep. of Germany ....... 3143920

[51] Int. Cl.³ .................... B01J 13/00; C09K 15/30; B01F 17/32
[52] U.S. Cl. ................................. 252/311; 252/401; 252/357; 568/448; 544/198
[58] Field of Search ............... 252/311, 401, 357; 568/448; 264/4.7; 544/198

[56] References Cited

U.S. PATENT DOCUMENTS

| | | | |
|---|---|---|---|
| 2,000,152 | 5/1935 | Walker | 568/422 |
| 2,002,243 | 5/1935 | Scott | 568/422 |
| 2,191,362 | 2/1940 | Widmer | 544/198 X |
| 2,237,092 | 4/1941 | Swain | 568/422 |
| 2,544,071 | 3/1951 | Dudley | 544/198 |
| 3,206,407 | 9/1965 | Lutwack | 544/198 X |
| 3,309,345 | 3/1967 | Lutwack | 544/198 X |
| 3,645,841 | 2/1972 | Cabestany et al. | 544/198 X |
| 4,028,334 | 6/1977 | Chalmers et al. | 544/198 X |
| 4,086,204 | 4/1978 | Cassandrini et al. | 544/198 X |
| 4,234,728 | 11/1980 | Rody | 544/198 |
| 4,315,859 | 2/1982 | Nikles | 544/198 X |
| 4,339,578 | 7/1982 | Werle | 544/207 |
| 4,400,505 | 8/1983 | Loffelman et al. | 544/198 |
| 4,409,348 | 10/1983 | Wiezer et al. | 544/198 X |

FOREIGN PATENT DOCUMENTS

| | | | |
|---|---|---|---|
| 14683 | 8/1980 | European Pat. Off. | 544/198 |
| 65169 | 11/1982 | European Pat. Off. | 544/198 |
| 1205071 | 11/1965 | Fed. Rep. of Germany . | |
| 1205073 | 11/1965 | Fed. Rep. of Germany . | |
| 2138309 | 2/1973 | Fed. Rep. of Germany . | |
| 2358856 | 5/1975 | Fed. Rep. of Germany . | |
| 2919496 | 12/1980 | Fed. Rep. of Germany . | |
| 22347 | 3/1981 | Japan . | |

OTHER PUBLICATIONS

Kaiser, J. Amer. Chem. Soc., vol. 73, pp. 2984–2986, (1951).
Walker, Formaldehyde, 3rd edition, p. 95.

*Primary Examiner*—Richard D. Lovering
*Assistant Examiner*—Catherine S. Kilby
*Attorney, Agent, or Firm*—Cushman, Darby & Cushman

[57] ABSTRACT

There is described new alkylene bismelamines and their production. They correspond to the formula

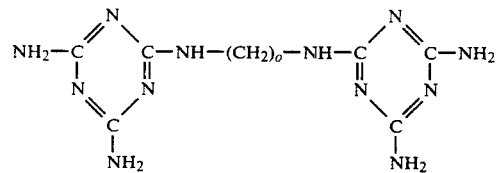

in which o is a number from 10 to 18. Alkylene bismelamines serve as stabilizers for formaldehyde solutions and as such have an outstanding suitability and activity.

13 Claims, No Drawings

BISMELAMINE STABILIZERS

BACKGROUND OF THE INVENTION

The invention is directed to new bismelamines and the use of bismelamines for the stabilization of formaldehyde.

There are known alkylene bismelamines of the formula

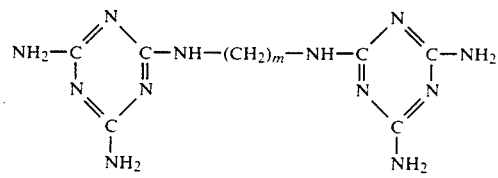

in which m is a number from 1 to 10, see Dudley U.S. Pat. No. 2,544,071, e.g. Example 10. Dudley also shows using octadecamethylenediamine as a starting material in making his polymelamines. Kaiser, J. Amer. Chem. Soc. Volume 73, pages 2984–2986 shows ethylene bismelamine.

SUMMARY OF THE INVENTION

In one aspect of the present invention there are prepared new alkylene bismelamines of the formula

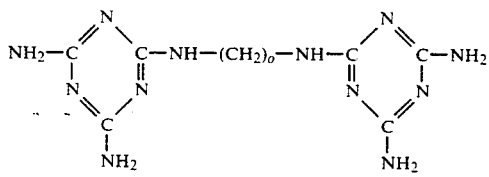

in which o is a number from 10 to 18 inclusive.

The alkylene bis melamines of the invention can be produced in the same manner as the known alkylene bismelamines, for example by reaction of the corresponding aliphatic diamine with 2-chloro-4,6-diamine-1,3,5-triazine corresponding to the process according to Dudley U.S. Pat. No. 2,544,071 or according to Kaiser, J. Amer. Chem. Soc. Vol 73 (1951) pages 2984–2986. For example, for the production of decamethylene bismelamine the starting material is 1,10-diaminodecane, for the production of dodecamethylene bismelamine the starting material is 1,12-diaminododecane, for the production of tetradecamethylene bis melamine the starting material is 1,14-diaminotetradecane and for the production of hexadecamethylene bismelamine the starting material is 1,16-diaminohexadecane.

Aqueous formaldehyde solutions, especially solutions having a formaldehyde content above 30 weight percent are unstable if the temperature at which they are stored falls below a certain minimum. There occurs turbidity through the formation of formaldehyde oligomers and finally the precipitation of paraformaldehyde. The higher the concentration of formaldehyde and the lower the storage temperature the more unstable are the solutions. Accordingly to the data in the monograph "Formaldehyde" by J. F. Walker, 3rd edition, page 95, a 30 percent formaldehyde solution remains stable for up to about 3 months if it is held at at least 7° C. For a 37 percent solution the required minimum temperature is 35° C., for a 45% solution 55° C. and for a 50% solution 65° C. However, a disadvantage of the use of higher storage temperature is that formic acid forms to a considerable extent in the formaldehyde solutions. This causes corrosion and is particularly disturbing in the use of formaldehyde solutions for condensation reactions.

The above mentioned values refer to formaldehyde solutions which contain less than 1 weight percent methanol as a stabilizer. To be sure by using higher methanol concentrations there can be produced equal storability at lower temperature, but there are required disproportionately high methanol concentrations. For example there is needed in a 37 percent formaldehyde solution for a storage temperature of 21° C., a methanol content of 7%, for 7° C. a methanol content of 10% and for 6° C. a methanol content of 12%. The addition of methanol, however considerably increases the cost of the formaldehyde solutions, especially since the methanol is generally lost in using the solutions. Apart therefrom through the methanol the speed of reaction in numerous condensation reactions, for example in the condensation with melamine, is reduced.

Besides methanol there are known as stabilizers (for formaldehyde), ethanol, propanol-1, propanol-2, ethylene glycol, glycerine, urea, methyl urea, dimethyl urea, thiourea, diethyl thiourea, formamide, melamine, methylol melamine and acetoxime (J. F. Walker "Formaldehyde", third edition, page 95, U.S. Pat. No. 2,000,152, U.S. Pat. No. 2,002,243, and Swain U.S. Pat. No. 2,237,092). However, these materials must be used in concentrations of at least 2% to be effective.

There are also used as stabilizers 2,4-diamino-1,3,5-triazines or their methylol derivatives which contain a phenyl group or an aliphatic group with 7 to 9 carbon atoms in the 6-position, especially capric guanamine (German AS No. 1205071) and German AS No. 1205073). (Higher and lower alkyl guanamines were less effective.) The effect of these stabilizers is increased by additionally employing hydrophilic polyglycol ethers of fatty alcohol or of polyalcohol-fatty acid partial esters (German AS No. 2138309). However, even in these cases the effect of the stabilizers is unsatisfactory. Besides, the formaldehyde solutions stabilized in this manner are inclined to foam strongly.

Furthermore it is known to employ phenylene bisguanamines as stabilizers (German AS No. 2358856). To be sure these materials display a useful action. However, they are relatively difficult to obtain and especially have the disadvantage that they are only soluble with difficulty. Therefore it is hard and requires much time to bring the required amount of stabilizer into soluble form.

Finally it is known to use as stabilizers alkylene bisguanamines (German OS No. 29194 96 and related Werle U.S. Pat. No. 4,339,578. The entire disclosure of Werle is hereby incorporated by reference and relied upon). Indeed these materials have a suitable stabilizing effect and have good solubility in formaldehyde solutions and therefore are easy to handle, but they are difficult to obtain.

There has now been found a process for the stabilization of formaldehyde solutions which is characterized by employing as stabilizing agents alkylene bismelamines of the formula

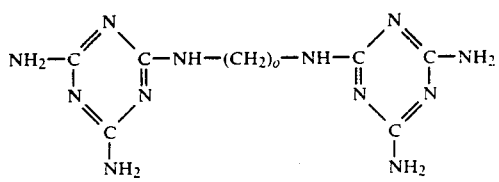

in which o is a number from 10 to 18. These compounds at the same concentration show a better action than all material previously used for this purpose. The alkylene bismelamines have relatively good solubility and therefore are easy to handle.

According to the invention there are employed as stabilizers the alkylene bismelamines in which according to the formula o is a number from 10 to 18, preferably a number from 11 to 14, especially 12.

The amount of the stabilizers to be added to the formaldehyde solutions depends, in a given case, to a certain extent on the formaldehyde contents and the storage temperature of the solutions. In most cases there are employed stabilizer contents between 0.001 and 0.1 weight percent. Preferably there are chosen stabilizer contents between 0.005 and 0.05, especially between 0.01 and 0.03 weight percent.

Unless otherwise indicated all parts and percentages are by weight.

The compositions can comprise, consist essentially of, or consist of the stated materials.

DETAILED DESCRIPTION

EXAMPLES

A. Production of the Alkylene Bismelamines

EXAMPLE 1

There were added 200 grams (1.0 mole) of 1,12-diaminododecane to a suspension of 291 grams (2.0 moles) of 2,4-dichloro-6-aminotriazine-1,3,5 in 500 ml of water. The pH of the mixture was adjusted to 8.5 by addition of a 50% aqueous sodium hydroxide solution. The mixture was heated to boiling with stirring and held at the boiling temperature under reflux for 2.5 hours, then cooled and filtered. The filter residue was washed with water until it was free from chloride ions. There remained 388 grams of pure dodecamethylene bismelamine, corresponding to a yield of 95%. The melting point (decomposition point) of the material was 182° to 185° C. The elemental analysis gave (in parantheses are given the calculated values for $C_{18}H_{34}N_{12}$); 52.1 (51.7)% C; 8.0 (8.2)% H; 39.9 (40.2)% N. The dodecamethylene bismelamine was identified by IR and NMR spectroscopically as well as by mass spectrograph.

EXAMPLE 2

The procedure was as in Example 1 but there were employed 228 grams (1.0 mole) of 1,14-diaminotetradecane. There were obtained 397 grams of tetradecamethylene bismelamine, corresponding to a yield of 91%. The melting point (decomposition point) of the material was 150° C. The elemental analysis gave (in parantheses are given the calculated values for $C_{20}H_{38}N_{12}$): 54.3 (53.8)% C; 8.2 (8.8)% H; 37.5 (37.6)% N.

In addition to IR and NMR spectroscopic analysis the tetradecamethylene bismelamine was identified mass spectroscopically.

B. Stabilization of the Formaldehyde Solutions

There were used formaldehyde solutions with various contents of formaldehyde. There were added to these solutions different amounts of bismelamines and other materials as stabilizers and there was tested how long these solutions were stable at specific storage temperatures.

To dissolve the stabilizers in the formaldehyde solutions these were held in each case 20 to 30 minutes with stirring at 80° C., except for isophthalobisguanamine which was held 120 minutes at this temperature.

The results are collected in the following tables. The stabilizer contents are given in weight percents, based on the total formaldehyde solution. As storability there is considered the time in which the solution was stable. The solutions were regarded as stable until the first just perceptible deposition occurred.

TABLE 1

Solutions having 37 weight percent formaldehyde and 0.40 weight percent methanol:

| Stabilizer Type | Content | Storage Temperature °C. | Storability Days |
| --- | --- | --- | --- |
| Decamethylene bismelamine | 0.01 | 0 | 12 |
| Dodecamethylene bismelamine | 0.01 | 0 | 28 |
| Tetradecamethylene bismelamine | 0.01 | 0 | 30 |
| Capric-guanamine | 0.01 | 0 | 4 |
| Dodecano-bis guanamine | 0.01 | 0 | 10 |
| Isophthalo-bisguanamine | 0.01 | 0 | 10 |

TABLE 2

Solutions having 40 weight percent formaldehyde and 0.50 weight percent methanol:

| Stabilizer Type | Content | Storage Temperature °C. | Storability Days |
| --- | --- | --- | --- |
| Decamethylene bismelamine | 0.03 | 0 | 6 |
| Dodecamethylene bismelamine | 0.03 | 0 | 15 |
| Tetradecamethylene bismelamine | 0.03 | 0 | 18 |
| Capric-guanamine | 0.03 | 0 | 4 |
| Dodecano-bisguanamine | 0.03 | 0 | 8 |
| Isophthalo-bisguanamine | 0.03 | 0 | 7 |

TABLE 3

Solutions having 50 weight percent formaldehyde and 0.55 weight percent methanol:

| Stabilizer Type | Content | Storage Temperature °C. | Storability Days |
| --- | --- | --- | --- |
| Decamethylene bismelamine | 0.015 | 39 | 8 |
| Dodecamethylene bismelamine | 0.010 | 39 | 12 |
| | 0.015 | 39 | 30 |
| | 0.020 | 35 | 60 |
| Tetradecamethylene bismelamine | 0.010 | 39 | 16 |
| | 0.015 | 39 | 30 |

What is claimed is:

1. An aqueous formaldehyde solution stabilized with a stabilizingly effective amount of an alkylene bismelamine of the formula

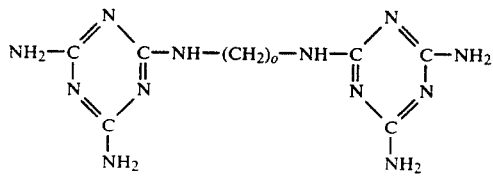

where o is an integer from 10 to 18.

2. An aqueous solution according to claim 1 containing methanol, the methanol being present in an amount of less than 1 weight %.

3. An aqueous formaldehyde solution according to claim 1 wherein o is an integer from 12 to 16.

4. An aqueous solution according to claim 3 wherein o is an integer from 12 to 14.

5. An aqueous solution according to claim 3 where o is 12.

6. An aqueous solution according to claim 3 wherein o is 14.

7. An aqueous solution according to claim 3 which contains 0.001 to 0.1 weight percent of the alkylene bismelamine.

8. An aqueous solution according to claim 7 wherein o is an integer from 12 to 14.

9. An aqueous solution according to claim 7 which contains 0.005 to 0.05 weight percent of the alkylene bismelamine.

10. An aqueous solution according to claim 9 where o is an integer from 12 to 14.

11. An aqueous solution according to claim 9 which contains 0.01 to 0.03 weight percent of the alkylene bismelamines.

12. An aqueous solution according to claim 11 wherein o is an integer from 12 to 14.

13. An aqueous solution according to claim 3 containing 30 to 50 weight percent of formaldehyde.

* * * * *